United States Patent [19]

Ackermann et al.

[11] Patent Number: 4,568,520

[45] Date of Patent: Feb. 4, 1986

[54] APPARATUS FOR THE AUTOMATED PRODUCTION OF A SERIES OF SAMPLES FOR THE ANALYSIS OF MIXTURES

[75] Inventors: Fritz Ackermann; Anton Bill, both of Zurich, Switzerland

[73] Assignee: Ismatec SA, Zurich, Switzerland

[21] Appl. No.: 577,626

[22] PCT Filed: Mar. 24, 1983

[86] PCT No.: PCT/CH83/00038

§ 371 Date: Jan. 31, 1984

§ 102(e) Date: Jan. 31, 1984

[87] PCT Pub. No.: WO83/04309

PCT Pub. Date: Dec. 8, 1983

[30] Foreign Application Priority Data

Jun. 5, 1982 [CH] Switzerland ............... 3485/82

[51] Int. Cl.[4] .......... G01N 1/28; G01N 35/00; B01D 29/02
[52] U.S. Cl. ............................ 422/66; 73/863; 73/863.23; 210/351; 210/387; 210/406; 422/100; 422/101; 436/44; 436/177; 436/180
[58] Field of Search ............... 422/66, 100, 101; 436/44, 177, 179, 180; 210/350, 351, 387, 400, 406; 73/863.23, 863, 864.81

[56] References Cited

U.S. PATENT DOCUMENTS

| | | | |
|---|---|---|---|
| 3,244,287 | 4/1966 | Staunton et al. | 210/406 X |
| 3,554,700 | 1/1971 | Maxon | 436/44 |
| 3,923,463 | 12/1975 | Bagshawe et al. | 422/66 |
| 3,940,250 | 2/1976 | Plakas et al. | 422/52 X |
| 4,167,875 | 9/1979 | Meakin | 210/387 X |
| 4,341,735 | 7/1982 | Seifried | 422/66 |
| 4,395,493 | 7/1983 | Zahniser et al. | 422/66 X |

FOREIGN PATENT DOCUMENTS 2241646 3/1974 Fed. Rep. of Germany.
2324056 11/1974 Fed. Rep. of Germany.

*Primary Examiner*—Barry S. Richman
*Assistant Examiner*—Robert J. Hill, Jr.

[57] ABSTRACT

Apparatus for manufacturing a series of samples of a mixture comprises a continuous filter strip on a roll and means for advancing the filter strip along a predetermined guide path. A suction head is located below the guide path and a bell member above the guide path at a point opposite to that of the suction head. The bell member is capable of being raised and lowered so that a portion of the filter strip is sealed between the bell member and suction head when the bell member is in the lowered position. Feeding means are provided through which samples of the mixture are conveyed from a sample vessel, through the bell member and onto the filter strip when the bell member is in the lowered position. A stamping device is located downstream the bell member whereby portions of the filter strip supporting the sample are stamped out in disc form. The disc is received within a receiving vessel. Reagent fluid supplied to the disc through a needle. The needle also conveys the disc from the stamping means to a sample receiving vessel.

5 Claims, 1 Drawing Figure

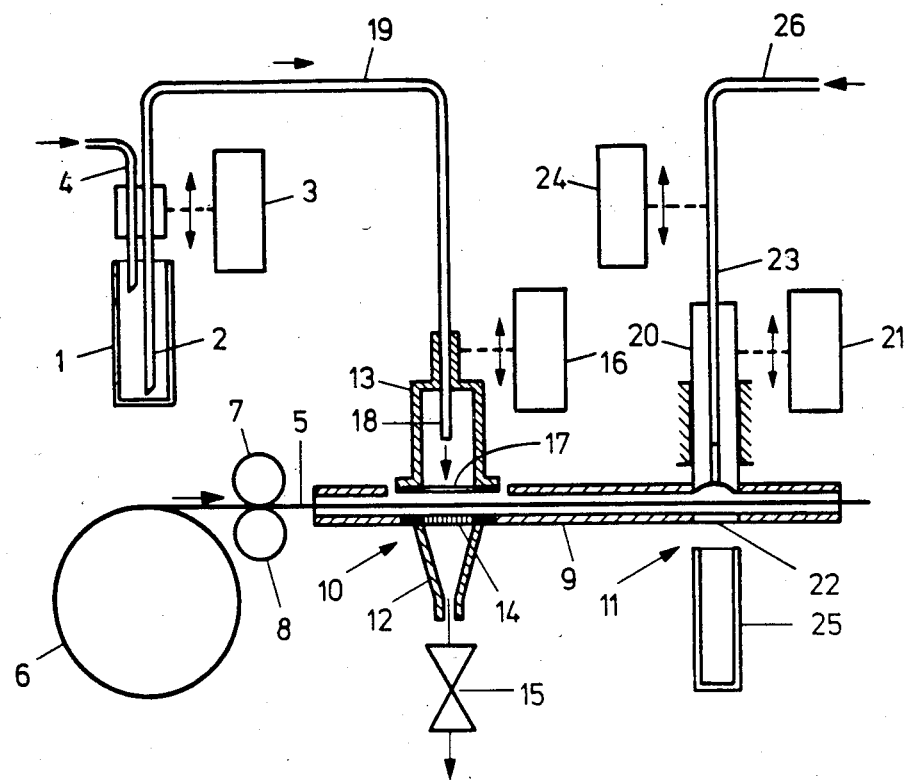

APPARATUS FOR THE AUTOMATED PRODUCTION OF A SERIES OF SAMPLES FOR THE ANALYSIS OF MIXTURES

The invention relates to a process for the production of a series of samples for the analysis of mixtures, in which the mixture in each case is taken from a container with liquid sample and deposited in places on a filter strip. The filtrate no longer needed is sucked off from the back of the filter strip and the filter residue is prepared for the analysis.

Such processes are used, for example, for the preparation of samples for immunological analysis or for the analysis of substances suspended in liquids or gases.

In a known process of this type there is provided a filter strip which is supported on a carrier band of stable material provided in places with windows. The samples can be shielded from contamination by covering them on both sides and stored after rolling up the carrier band. Such a filter strip with carrier band is suitable only for dry samples; moreover, material and production costs are high. Further, in this process the mixture to be filtered is pipetted onto the filter strip and without use of special protective measures there is a danger of contamination. Moreover, for the feed of the mixture to the pipette an additional conveying pump is required. The feed path is thus lengthened and the use of slowly operating tube pumps results in an increase in the duration of the mixture transport time. This may lead to changes in property or character of the sample batch. Additionally, a longer feed path is more expensive to clean between the successive sample throughputs.

An object of the invention is to provide a process of the type mentioned above wherein shorter throughput times and a reduction in the danger of contamination are acheived. Such a process eliminates many of the disadvantages outlined above.

Conveying the mixture by a suction force acting on the filter output eliminates the need for a pump in the feed path. The feed path can thereby be kept shorter, which makes possible a more rapid throughput and facilitates the cleaning.

Moreover, a substantially complete seal at the place where the sample is filtered (the filter place) offers protection against any substance exchange with, or contamination from, the environment. The portions of the filter strip supporting the mixture deposited are each stamped out and transferred into sample vessels. The filter strip used in the present invention therefore need not be as strong as that used in the prior art since there is no longer storage of the entire filter strip with the mechanical stresses associated therewith. For the same reason it is possible to dispense with a carrier band.

A process which operates with unreinforced filter strips is also known. However, the filter strips are cut by hand into a number of parts each incorporating a filter place and introduced into the sample vessels. Contamination and errors, however, are difficult to avoid in this process, and the handling is both complicated and time-consuming.

A further aspect of the invention is the provision of apparatus for the manufacture of a series of samples for the analysis of mixtures.

BRIEF DESCRIPTION OF THE DRAWING

In the drawing there is schematically represented an embodiment of the apparatus of the invention. It can be a matter here of a separately constructed filtering station which can be used in an automatically operating analysis installation for series analysis.

The prepared and possibly pretreated sample batches are present in open or closed containers, which, for example, are moved forward stepwise in series and are supplied successively to the filtering station illustrated. As shown in the drawing, a sample vessel is moved to to the point where the process commences.

For the successive removal of the sample batches from the batch vessels 1, there is provided a raisable and lowerable cannula 2, which is connected to a hoisting motor 3. A pipette 4 is mechanically connected adjacent the cannula 2 for supplying any possible additional material including the cleaning fluid.

The filter strip 5, which is made of glass fiber, is taken from a roll 6 and moved forward stepwise by advance rolls 7, 8 along a guide path 9. Along the guide path 9, there is a filtering device 10 and a stamping device 11.

The filtering device 10 consists of a suction head 12 arranged underneath the guide path 9 and a vertically movable bell 13 arranged above the guide path 9 and opposite the suction head 12. The suction head 12 is closed off at the height of the guide path 9 by a filter carrier 14, which may be in the form of a sinter glass plate, and is connected over a controlled valve 15 with a vacuum pump (not represented). The bell 13 is connected to a hoisting motor 16 which can press the bell 13 against the suction head 12 onto the intermediately lying filter strip 5, so that the filter place is sealed off on both sides. On the lower edge of the bell 13 there may be provided a sealing ring 17. In the bell 13 there is installed a line 18 with an elevationally adjustable mouth, directly connected via a tube 19 with the cannula 2.

The stamping device 11 comprises a stamping die 20 and a hoisting motor 21 for its operation. At the stamping opening 22 in the guide path 9 there is stamped out in each case a small disk of the filter strip 5. A stop needle 23 moveable by a hoisting motor 24 conveys the stamped-out disk into a sample receiving vessel 25 which, in turn, is moved onward stepwise in a chain of receiving vessels. Reagent fluid is fed to the the stop needle 23 through a tube 26.

The filtering station operates in rhythm with the advance devices (not represented) for the transport of the batch vessels 1 and of the receiving vessels 25. For the operation, there may be provided a program control system which controls the activity of the hoisting motors 3, 16, 21, 24, the advance rolls 7, 8 and the valve 15 and may be set in motion and halted by the first and the last vessel of a series of sample batch vessels.

Operation of the filtering station is as follows:

In the rest state, all the hoisting motors 3, 16, 21, and 24 are in the upper position, and the valve 15 is closed or stands on ventilation.

As soon as he first sample batch vessel 1 reaches the cannula 2, the cannula is lowered into the batch vessel 1 and the bell 13 is lowered onto the filter strip 5 which comes to a standstill. At this stage, buffer solutions may be added through pipette 4. Before the end of this addition, the valve 15 is opened, causing the suction force of the vacuum pump to become operative and the sample batch from the batch vessel 1 is conveyed from the cannula 2 through the tube 19 to the filter place inside the bell 13. Since there is no pump between cannula 2 and bell 13, the transfer takes place within a few seconds, so that the duration of the effect of any buffer solution on the sample can be kept within desired limits. Following upon this, cleaning fluid is introduced in doses through the pipette 4. The whole mixture is filtered and the filtrate is led off over the suction head 12. In this process the line 18 is adjusted in height with repect to the bell 13 in such a way that the mouth does not come into contact with the mixture collecting at the filter place. After the cleaning, the cannula 2 and the bell 13 are again lifted, and the valve 15 is closed.

The vessels 1 and 25 and the filter strip 5 are now advanced by one step, so that the next batch vessel 1 comes into the taking position, the first sample receiving vessel 25 comes into the receiving position and the filter place occupied with the filter residue comes to stand under the stamping die 20.

A disk incorporating the occupied filter place is stamped out of the filter strip 5 with the stamping die 20, and conveyed by the stop needle 23 into the receiving vessel 25. During the withdrawal of the stop needle 23, the reagent fluid is supplied through the tube 26. The reagent fluid may be a scintillation fluid in the case of radioimmunological samples. The end of the stop needle 23 is preferably widened in trumpet form, so that the filter disk is gripped as near to its edge as possible, and cannot come in contact with the outside of the stop needle during the introduction into the receiving vessel 25. The reagent fluid serves simultaneously for the cleaning of the stop needle.

The supply of the various fluids through the pipette 4 and the tube 26 preferably occurs through switch operated dispensers.

The hoisting motors 3 and 16 can be replaced with a single hoisting motor in the case of a suitable arrangement of the cannula 2 and of the bell 13.

For pressing of the bell 13 onto the filter strip 5, there is preferably provided an excess pressure spring.

The stamping out of the filter disk and the filtering of the next sample can take place simultaneously.

We claim:

1. Apparatus for the manufacture of a series of samples of a mixture, the apparatus comprising:
   a guide path;
   a continuous filter strip;
   means for intermittently advancing the filter strip along the guide path;
   a suction head located below the guide path at a first position along said guide path;
   a movable bell member located above the guide path at said first position and opposite the suction head and capable of being raised and lowered to an upper and lower position so that a portion of the filter strip is sealed between the moveable bell member and the suction head when the moveable bell member is in the lower position;
   feeding means for conveying a sample of a mixture by suction pressure to the suction head through the moveable bell member to deposit the sample onto the sealed portion of the filter strip when the moveable bell member is in the lower position;
   stamping means located above the guide path at a second position along said guide path downstream from said first position for stamping out the portion of the filter strip on which the sample has been deposited; and
   sample receiving means located below the guide path at said second position and opposite said stamping means for receiving the stamped out portion of the filter strip, said stamping means further including means for conveying the stamped out portion of the fulter strip to the sample receiving means and supplying reagent fluid to the sample receiving means.

2. Apparatus as claimed in claim 1 wherein the stamping means is such that it stamps out disc shaped portions from the filter strip.

3. Apparatus as claimed in claim 1 wherein the sample receiving means comprises a receiving vessel.

4. Apparatus as claimed in claim 1 wherein the means for conveying the stamped out portion of the filter strip to the sample receiving means and supplying reagent fluid to the sample receiving means comprises a stop needle operatively connected to a reagent fluid supply line.

5. Apparatus as claimed in claim 4 wherein one end of the stop needle is widened so as to contact the stamped out portion of the filter strip as near to its edge as possible.

* * * * *